United States Patent [19]

Olson

[11] 4,170,229

[45] Oct. 9, 1979

[54] METHOD FOR IMPROVED HEALTH CARE OF HAIR AND SCALP USING A VITAMIN A AQUEOUS EMULSION

[75] Inventor: B. Newell Olson, Norwich, N.Y.

[73] Assignee: Dominion Pharmacal, Inc., Norwich, N.Y.

[21] Appl. No.: 869,774

[22] Filed: Jan. 16, 1978

[51] Int. Cl.$^2$ .................. A61H 7/00; A61K 31/07; A61K 31/195
[52] U.S. Cl. .................. 128/67; 424/DIG. 4; 424/273 R; 424/319; 424/344
[58] Field of Search ............. 424/DIG. 4, 273 R, 319, 424/344; 128/67

[56] References Cited

U.S. PATENT DOCUMENTS

| 2,417,299 | 3/1947 | Freedman et al. | 424/344 X |
| 3,729,568 | 4/1973 | Kligman | 424/344 X |
| 4,021,574 | 5/1977 | Bollag et al. | 424/324 |

FOREIGN PATENT DOCUMENTS

| 2050658 | 5/1972 | Fed. Rep. of Germany | 424/344 |
| 1297730 | 5/1962 | France | 424/344 |
| 1586682 | 1/1970 | France | 424/319 |
| 1603799 | 5/1971 | France | 424/319 |
| 996207 | 6/1965 | United Kingdom | 424/344 |

OTHER PUBLICATIONS

Neumann, Soap, Perfumery and Cosmetics, vol. XL, No. 4, pp. 272, 276 and 278.

*Primary Examiner*—James O. Thomas, Jr.
*Assistant Examiner*—Vera C. Clarke

[57] ABSTRACT

This invention relates to Vitamin A-containing crystal clear transparent aqueous sprayable emulsions for application to hair and scalp according to a spray-on then brush-in technique which has been found to effectively reduce itching, flaking of common dandruff and seborrhea, condition the hair and scalp, and, in some instances, reduce excessive falling hair.

3 Claims, No Drawings

METHOD FOR IMPROVED HEALTH CARE OF HAIR AND SCALP USING A VITAMIN A AQUEOUS EMULSION

BACKGROUND OF THE INVENTION

Crystal clear transparent emulsions of lanolin are described in the prior art such as in U.S. Pat. No. 3,052,609. Crystal clear aqueous solutions of higher fatty alcohols and higher fatty alcohol esters are described in U.S. Pat. No. 3,052,607. In the present invention, a method has been found to provide crystal clear transparent emulsions of Vitamin A as the primary active ingredient and Vitamin A in aqueous combination with thio-amino acids and thio-amino complexes with allantoin.

Vitamin A has a well established chemical structure. It is commercially available from a variety of sources. One such source is Roche Chemical Company of Nutley, New Jersey. Vitamin A is considered to be insoluble in water. Notwithstanding the widespread use of Vitamin A in ointment bases, cosmetics and topical pharmaceutical preparations, until the present invention, all Vitamin A-containing aqueous compositions comprised cloudy emulsions and grease-like masses. Application of these type materials to the hair and scalp have enjoyed limited use due to the greasy, and often messy, after-effect of their use. Consequently, hair and scalp problems of major importance to numerous people have received limited treatment.

A hair and scalp problem of widespread importance is the itching, scaling and sloughing of epidermal cells of the scalp referred to as common dandruff. "Dandruff" is known to be a complex condition. At the present time, it is believed that a dandruff condition involves several factors such as the presence of Staphylococcus aureus and Pityrosporum ovale skin bacteria along with oily, dead, surface epidermal cells. Growth of these microbes is believed to promote, or at least to be associated with, the itching, scaling and unpleasant appearance associated with increased desquamation of epidermal cells. Heretofore, successful anti-dandruff compositions have involved use of germicides in detergent bases many of which can be very harsh to the skin, hair and eyes.

Disorders of the scalp can also include a condition known as *Seborrhea Capitis*. This involvement is characterized by thick, yellowish greasy scales of the vertex and possibly covering most of the scalp. In many cases the hair may be matted with crusts. These crusts may vary in color. They frequently have a dirty, waxy appearance and comprise a most distressing cosmetic problem. When the scaling is dry it is given the medical diagnosis of *Pityriasis sicca* and when the scaling is oily, it is given the diagnosis of *Pityriasis oleosa*. Since there is no known cure for seborrhea type disorders, treatment must by necessity be aimed at the most effective method that will achieve symptomatic relief. Effective means of control should include a means for cleaning and clearing the scalp scales and oiliness. A suitable remedy will need to be non-irritating, non-sensitizing, non-toxic and non-oily since this condition is normally brought on by excessive oiliness.

Conditioning of the hair is often essential to good grooming. This is particularly the case if the hair is of fine texture or excessively dry. In other instances, conditioning is used when hair has become brittle or straw-like due to excessive use of hair dyes, bleaches and the like. With the advent of blow-dryers for the hair, excessive exposure to heat can leave the hair in a limp and tortured state. Conditioners in common use comprise protein-enriched lotions, creams and numerous oil-based materials which are applied to the hair followed by rinsing to remove excess conditioner. The degree with which hair absorbs the conditioner varies both with the conditioner used and the state of the hair. Most, if not all, conditioners have a tendency to leave the hair with an oily-greasy feel which can be undesirable. The primary reason for this is that the amount of conditioner applied is in excess of the amount absorbed by each hair strand.

In literature publications such as in the Journal of the Society of Cosmetic Chemists of Great Britain, Vol. 10, Number 4, (1959) under an article entitled "The Sorption of Amino Acids from Shampoo on to Hair", by Herd, J. K., et al, it was demonstrated that amino acid sorption on to the hair occurs in a very uneven manner. Wide variation is noted along the hair shaft as determined at intervals outward from the root end. In order for effective conditioning of hair and improvement in manageability, even distribution of sorbed materials is desirable. Heretofore, no simple or economic means for accomplishing this objective has been available.

Disorders of the scalp can lead to a widespread problem known as "falling hair". Causes of this problem are not yet fully understood. While it is believed that heredity plays a major role, it is generally considered that this factor is not the only one at work. Other factors such as stress, poor nutrition and excessive oiliness of the scalp are also believed to be involved in the cause and effect of this problem.

Accordingly, the present invention has as its object to provide a method and composition for effectively controlling the itching, flaking and unsightly desquamation of epidermal cells referred to as common "dandruff".

It is another object of the invention to provide a method and composition for effectively controlling the oiliness of the scalp normally associated with *Seborrhea Capitis*.

It is still another object of the invention to provide a method and composition which are capable of effectively applying a non-greasy conditioner to individual strands of human hair in a manner of even distribution such that the hair acquires improved body, texture, shine and manageability.

It is a still further object of the invention to provide a method and composition which, in some instances at least, can effectively reduce the amount of falling hair in some persons.

SUMMARY OF THE INVENTION

This invention provides a crystal clear transparent aqueous emulsion of Vitamin A, singly or in combination with other active ingredients shown in the claims hereof which can be sprayed on to the hair and scalp as a fine mist and then brushed in with a conventional hand-held hair brush to yield even distribution of the emulsion throughout the hair and scalp. By application of inventive compositions in this manner, unexpected benefits accrue to hair and scalp. Heretofore, attempts to apply meaningful grooming aids, medicaments, hair beautifiers, hair and scalp conditioners and the like to human hair and scalp have been carried out by incorporating these type ingredients into bases and/or carrying materials such as shampoos, after-shampoo rinses, ointments, cloudy emulsions, pastes and the like. In so doing, all such applications have had very limited acceptability. In the present invention, the degree of benefit achieved through use of very low concentrations of active ingredients without need for conventional bases and carrying materials has been totally unexpected. It has been found that very low concentrations of active ingredients will achieve superb results through use of the present compositions thus minimizing the amount of undesirable materials being put on to the hair and scalp to achieve these benefits. In addition, it has been totally unexpected the degree with which uniform distribution of materials to individual hairs of the human head occurs through use of the inventive process. While not wanting to be bound by any technical explanation herein, it is believed that the sprayable crystal-clear transparent emulsions are benefited by the apparent electrostatic charge generated in the hair brushing process with a hand held hair brush. It thus appears, for example, that the uniformity of distribution is directly related to the degree of electrostatic charge generated on the surface of individual hairs by this process. It will be apparent therefore, that the present invention overcomes a defect encountered in all previous attempts to apply various treatments to the hair and scalp. By the process of the present invention, in combination with use of the present crystal-clear transparent aqueous emulsions, effective ingredients for varied medicinal, beautifying and other purposes can now be applied to the hair and scalp in a manner exercising maximum potential from these ingredients while overcoming negative aspects of inefficient use of unwanted materials and the undesirable nature of applying unwanted materials to hair and scalp.

In preparing the crystal-clear emulsions of this invention highly purified Vitamin A should preferably be used such as Vitamin A palmitate available from Roche Chemical Company of Nutley, New Jersey under the designation PIMO/BH. To effect the emulsion, critical ratios of Vitamin A and emulsifier for the Vitamin A are employed. Water is then added in a special two-step proces in order to achieve a stable, crystal-clear transparent system. Also, the time/temperature relationship for the addition of the water to the Vitamin A-emulsifier system is critical. Suitable emulsifiers, also having the capacity in some instances to function as partial solubilizers for the Vitamin A have been found to be surfactants such as polyoxyethylene fatty ethers available commercially under the trade name of "BRIJ" emulsifiers from ICI America, Inc., of Wilmington, Delaware. Preferred members of this group include polyoxyethylene cetyl ether, polyoxyethylene stearyl ether and polyoxyethylene oleyl ether. Other suitable emulsifiers comprise polyoxyethylene sorbitan fatty acid esters such as the "Tween" compounds available also from ICI America. Preferred members of the group include polyoxyethylene sorbitan monolaurate, polyoxyethylene sorbitan monopalmitate, polyoxyethylene sorbitan monostearate, and polyoxyethylene sorbitan monooleate.

PREFERRED EMBODIMENT OF THE INVENTION

The preferred method of preparing the crystal-clear emulsions of this invention comprises first mixing together Vitamin A and emulsifier in an amount ranging from 1 part Vitamin A to from 4 to 8 parts emulsifier. The mixture is then warmed to a temperature of from 35 to 40 degrees Centigrade. Water, which has been preheated to the same temperature, is then added very slowly while maintaining slow stirring. The amount of water added should be in the range of 1 part mixture to 6 to 8 parts water. After addition of the water over a time period of from 2 to 3 minutes, the batch is cooled to 25 degrees Centigrade and placed on hold until it clears of any turbidity. Following this, additional water having a temperature of about 25 degrees Centigrade can be added to yield the desired dilution for specific purposes. Failure to follow directions rather precisely can lead to a cloudiness within the batch which can adversely affect stability. Attempts to "clear" the batch in those instances when cloudiness has remained after this phase have all met with failure.

In preparing the cyrstal-clear emulsions, other water-insoluble materials can be included in the original mixture along with Vitamin A and emulsifier. These materials include fragrances, anti-oxidants such as butylated hydroxy anisole (BHA) available from Eastman Chemicals Company in Kingsport, Tennessee, preservatives such as propylparaben available from Tenneco Chemicals Company in Saddle Brook, New Jersey and anti-dandruff ingredients such as allantoin and derivatives thereof available from Schuylkill Chemical Company, in Philadelphia, Pennsylvania. Preferred derivatives of allantoin include allantoin N-acetyl cystine, allantoin N-acetyl cysteine, allantoin N-acetyl DL methionine, aluminum hydroxy allantoin N-acetyl cystine, aluminum hydroxy allantoin N-acetyl cysteine, aluminum hydroxy allantoin N-acetyl DL methionine and the like.

Water-soluble additives can be added to the water-soluble phase of the crystal-clear solutions without affecting the clarity of the product. These additives include conditioners, preservatives, colorants and pH adjusting agents. Preferred conditioners comprise collagen, gelatin, wheat germ, amino acids and derivatives thereof. Preferred amino acids comprise thio-amino acids such as cystine, cysteine, and methionine. Preferred thio-amino acid derivatives include N-acetyl cystine, N-acetyl cysteine, N-acetyl methionine and the like.

Suitable preservatives include methylparaben available from Tenneco Chemicals Company, in Saddle Brook, New Jersey. Suitable colorants are available commercially as FD&C and D&C colors. Adjustment of pH can be made using sodium hydroxide, potassium hydroxide or other alkaline materials. Acidifying agents can also be used. These include acetic acid, citric acid, potassium dihydrogen phosphate, and hydrochloric acid. Chelating agents can be employed for pH adjustment purposes. These can include ethylenediamine tetraacetic acid or the alkali salt thereof such as disodium or tetrasodium.

The following specific examples are further illustrative of the nature of the present invention, but it is to be understood that the invention is not limited thereto. The compositions of these examples show amounts and proportions which are by weight unless otherwise specified.

EXAMPLE I

A crystal-clear water soluble solution of Vitamin A palmitate was obtained by mixing one part Vitamin A palmitate, five parts Brij 52, and one part propylparaben in a separate container and then warming to 40 degrees Centrigrade while stirring gently. Fifty six parts water, preheated to 40 degrees Centigrade, is then added very slowly over a three minute period while maintaining continued slow stirring. As soon as the water has been added, the batch is cooled to 25 degrees Centigrade and set aside for one hour to clear of turbidity and cloudiness. After the one hour period, five hundred parts water at 25 degrees Centigrade containing 1 part methylparaben is then added with continued slow stirring.

The final crystal-clear product is then placed in a plastic container equipped with a manually operated sprayer such as is available from Diamond International Corporation in New York, New York under the tradename of "Mistette". The clear solution is then sprayed on to the hair and scalp and brushed in with several gentle strokes using a conventional hand-held hair brush. The brush should be equipped with several rows of bristles of sufficient length and stiffness to penetrate the hair of the human head to reach the scalp surface.

EXAMPLE II

| Spray-on, Brush-in Crystal Clear Solution | | |
|---|---|---|
| | Ingredient | Amount |
| 1. | Vitamin A Palmitate | 0.12 |
| 2. | Tween 80 | 0.85 |
| 3. | BHA | 0.02 |
| 4. | Allantoin | 0.20 |
| 5. | Propylparaben | 0.16 |
| 6. | De-ionized water | 8.00 |
| 7. | De-ionized water | 90.45 |
| 8. | Methylparaben | 0.20 |

Add ingredients 1 through 5 in order of appearance to a separate container. Stir slowly while heating to 38 degrees Centigrade until clear homogenous solution results. Then add ingredient 6, de-ionized water preheated to 38 degrees Centigrade, to the container with continued slow steady stirring. After ingredient 6 has been added, the batch is set aside for one hour to clear of all turbidity. Ingredient 7, at approximately 25 degree Centigrade temperature, incorporating ingredient 8, is then added with slow stirring to complete the final product.

Apply the final product to hair and scalp according to the invention.

EXAMPLE III

| Spray-on, Brush-in Crystal Clear Solution | | |
|---|---|---|
| | Ingredient | Amount |
| 1. | Vitamin A Palmitate | 0.12 |
| 2. | Tween 60 | 0.84 |
| 3. | Fragrance | 0.10 |
| 4. | Brij 52 | 0.40 |
| 5. | Water | 8.00 |
| 6. | Water | 90.34 |
| 7. | N-acetyl DL Methionine | 0.20 |
| 8. | Sodium hydroxide (N/1) | q.s. |

Add ingredients 1 through 4 in order of appearance to a separate container. Stir slowly while heating to 40 degrees Centigrade until a clear homogenous solution results. Then add ingredient 5 preheated to 40 degrees Centigrade. After addition of ingredient 5 over a 3 minute period while maintaining steady slow stirring, the batch is cooled immediately to 25 degrees Centigrade by use of exposure to a cold water bath or cold water jacketed kettle. After approximately one hour, a solution made up of ingredients 6, 7 and 8 is added with continued slow stirring. Sufficient sodium hydroxide is added to the aqueous solution of ingredient 6 to yield a final pH of from 4.2 to 4.6.

Apply the final product to hair and scalp according to the invention.

EXAMPLE IV

Spray-On, Brush-In Crystal Clear Solution

A crystal-clear aqueous solution is prepared in accordance with Example III except that allantoin N-acetyl DL methionine is substituted for N-acetyl DL methionine.

CASE HISTORY NO. 1

White, male age 52 was having a problem with typical dandruff comprising itching, scaling and flaking. After one week of regular use of the composition of Example II according to the inventive process, no noticeable itching, scaling and flaking was perceived. The patient shampooed his hair at one week intervals using a non-anti-dandruff shampoo on a continuous basis which included before, during and after the test was in progress.

CASE HISTORY NO. 2

White, female, age 42 had a probelm of dry, brittle and unmanageable hair. After one week of regular use of the composition of Example III according to the invention, the hair was soft, manageable and fluffy.

CASE HISTORY NO. 3

White, male, age 51 was loosing approximately 50 to 60 head hairs each day as determined by wetting the hands and drawing the fingers, while in spread position, through the hair to remove loosened individual hairs. After 4 weeks of regular daily use of the composition of Example IV according to the inventive process, the daily loss of head hairs was reduced to approximately 12 to 20.

The use of the term "solution" in the aforementioned specification is not to be construed as meaning a true solution according to pure technical definition. It is rather to be construed as meaning a mixture which appears to the naked eye to be a solution, and accordingly, the word "solution" is to be construed as covering transparent emulsions.

The foregoing detailed specification has been given for the purpose of explaining and illustrating the invention. It is to be understood that the invention is not limited to detailed information set forth, and that various modifications can be made within each example herein provided without departing from the scope of the invention as defined by the appended claims.

I claim:

1. A method for treating conditions of hair and scalp to effect conditioning thereof and relief from dandruff symptoms, said method comprising spraying a fine mist of an aqueous emulsion in sufficient amount to effect moistening thereof and brushing said hair and scalp with a hand held brush having bristles, said brushing being carried out in sufficient number of strokes to effect even distribution thereof throughout said hair and scalp, said emulsion containing an effective amount of essential ingredient comprising Vitamin A palmitate and allantoin N-acetyl methionine.

2. Method of claim 1 wherein Vitamin A palmitate is present in the emulsion in the order of about 0.15% by weight.

3. Method of claim 1 wherein allantoin N-acetyl methionine is present in the emulsion in the order of about 0.2%.

* * * * *